United States Patent [19]

Pinier et al.

[11] Patent Number: 5,572,321
[45] Date of Patent: Nov. 5, 1996

[54] DETECTOR FOR MEASURING THE LUMINOUS INTENSITY SCATTERED BY THIN FILMS OF COLLOIDAL MEDIA

[75] Inventors: Frank Pinier, Cagnes S/Mer; Bill Woodley, Mons; Patrick Patin, Nice; Didier Frot, Choisy le Roi, all of France

[73] Assignees: Institut Francais du Petrole, Rueil-Malmaison; Sematech, Nice, both of France

[21] Appl. No.: 347,257

[22] Filed: Nov. 23, 1994

[30] Foreign Application Priority Data

Nov. 24, 1993 [FR] France .................................. 93 14347

[51] Int. Cl.⁶ .................................................. G01N 21/00
[52] U.S. Cl. ........................................ 356/338; 356/381
[58] Field of Search ...................................... 356/335, 336, 356/337, 338, 339, 340, 341, 342, 343, 300, 301, 381, 382

[56] References Cited

U.S. PATENT DOCUMENTS 3,621,243  11/1971  Olivier ..................... 356/335
4,940,326   7/1990  Tatsuno .................... 356/336
4,966,457  10/1990  Hayano et al. ............. 356/338
5,198,369   3/1993  Itoh et al. ................. 356/337

FOREIGN PATENT DOCUMENTS 0516481  12/1992  European Pat. Off. .
3700286   7/1987  Germany .
9105995   5/1991  WIPO .

Primary Examiner—Hoa Q. Pham
Attorney, Agent, or Firm—Antonelli, Terry, Stout & Kraus

[57] ABSTRACT

The present invention relates to a device for measuring the luminous intensity scattered by thin films of colloidal media. It is more particularly intended for submicron grain-size analysis by photon correlation, and comprises a device for measuring the luminous intensity scattered by thin films (16) of colloidal media. The invention includes a monochromatic luminous source (2); a converging optical system (4) focusing the source on the thin film to be analyzed; at least one photosensitive detector (5; 5'; 5''; 5''') detecting the light scattered or backscattered by the thin film; and a system (60, 70) for processing the signal coming from photodetector(s) (5).

30 Claims, 3 Drawing Sheets

DETECTOR FOR MEASURING THE LUMINOUS INTENSITY SCATTERED BY THIN FILMS OF COLLOIDAL MEDIA

BACKGROUND OF THE INVENTION

1. Field of the Invention

The present invention relates to a device for measuring the intensity of the light scattered by high concentrations of particles or macromolecules ranging between a plurality of nanometers and hundreds of microns. It is more particularly applied to photon correlation.

The present invention is more particularly directed to measuring the intensity of the light scattered by thin films of colloidal media.

2. Description of the Prior Art

Particle size measurements by quasi-elastic light scattering or photon correlation have been widely used for about 20 years. Particles or macromolecules of a diameter ranging between a plurality of nanometers and a plurality of microns may be characterized by this method which depends on RAYLEIGH's scattering theory.

To that effect, objects are introduced in a liquid (solvent or not) in a very low proportion. The prepared sample is introduced into a measuring cell which is traversed by a focused laser beam. The Brownian movement of the particles produces variations in time of the scattered light. These variations are directly proportional to the size of the particles.

The use of a suitable optical detector (spectrodiffusiometer, spectrogoniometer, etc.), a correlator and mathematical signal processing methods (Laplacian inversion, Fourier transform) thus allows a frequency distribution and therefore a size distribution of the particles to be known.

The theoretical analysis rests on the known hypothesis that each particle acts as an individual diffuser and there is no interactive effect between the particles, i.e. there is no "multiple scattering" which might limit or even prevent any interpretation of the variations of the observed scattered light.

Conventional submicronic grain-size analyses by photon correlation thus only analyze very low particle concentrations.

In order to remedy this drawback, a known solution is to introduce an optical fiber into the medium. The particles scatter light emitted at the end of the optical fiber. The light backscattered by the particles goes back through the optical fiber and reaches the photosensitive detector via a directional separator in order to prevent the source light from reaching the photodetector.

However, a certain amount of light is directly reflected from the fiber even before it comes out of it and reaches the detector. It must therefore be measured as a reference signal (heterodyne system).

Other means have been investigated, in the Field of backscattering with conventional cells. But, the reflection effects of the incident beam and the strong multiple scattering have not allowed useful results to be obtained. The conventional instruments for characterizing submicron particles by photon correlation as illustrated in FIG. 1 include a laser generator (not illustrated) generating a rectilinear laser beam 2. A cylindrical vessel or a vessel with parallel faces 3 containing a mixture of objects, particles or macromolecules (M) is arranged on the path of laser beam 2. The laser beam 2 is focused by means of a converging lens 4 on the center of this vessel. The objects (M) may be in solution or in suspension in the liquid. A detector 5 including an optical system and a photosensitive unit receives scattered light from the center of the vessel at an angle with respect to the axis XY. The photosensitive unit is then connected to a signal processing computer (not illustrated). The objects (M) are illuminated by scattered light from the beam 2. The Brownian movement of the objects produces variations in time of the scattered light. These variations are directly linked to the size of the objects and they may be studied, for example, by means of an analysis of the photon correlation spectroscopy type. In FIG. 2, it is easy to understand why this known device does not allow analysis of concentrated samples. In fact, as detector 5 observes a solution of objects (M) at an angle with respect to axis XY greater than 90° (backscattering), one receives, in addition to the characteristic direct scattering signal 6, the luminous rays due to the multiple scattering 7, and the rays from the reflection of laser 8 entering vessel 3. These latter parasitic luminous rays create a poor signal-to-noise ratio which makes it impossible to study the low variations cited above.

SUMMARY OF THE INVENTION

The object of the invention is to remedy the aforementioned drawbacks of the prior art and to obtain a homodyne signal, i.e. with no other reference signal. To that effect, the invention limits the effects of multiple scattering by using a very small scattering volume in the form of a thin film.

The present invention advantageously allows all the colloidal media to be better characterized in terms of its optical density, turbidity, viscosity and/or grain size.

It is well-known to perform grain size and turbidity measurements on colloids whose dense phase is weakly concentrated. However, the prior art does not allow such measurements to be performed on absorbent colloids.

One definite advantage of the invention is that it allows the whole of the measurements above stated to be performed on absorbent colloidal media, and notably grain-size, turbidity, optical density and viscosity measurements of the continuous phase.

The present invention may be particularly advantageously applied to viscosity measurements on thixotropic liquids, i.e. whose viscosity evolves when stress applied.

The invention thus relates to a device for measuring the intensity of the light scattered by thin films of colloidal media, including:

a monochromatic luminous source, a converging optical system focusing the source on the thin film to be analyzed, at least one photosensitive detector reacting to the light scattered or backscattered by the thin film, (electronic) means for processing the signal coming from the photodetector(s).

The optical system typically includes a dioptric element placed in the path of the luminous beam and one face which constitutes a first wall demarcating the thin film, and a second wall the demarcating thickness of the thin film The system according to the invention further includes a means for positioning the means opposite the wall the first of the dioptric element, i.e. intended for controlling the thickness of the thin film to be analyzed in order to reach the appropriate working points.

The dioptric element preferably includes a secant face so oriented that it reflects the beam coming from the luminous source, so that the beam passes through the thin film perpendicular to the wall face.

A photodetector is advantageously placed on an axis perpendicular to the secant face of the dioptric element, so as to observe an area surrounding the focusing point of the source where the luminous intensity scattered is generated.

According to an embodiment of the invention, the dioptric element may be a prism.

According to a method of operation of the invention, the luminous source and the prism are so arranged with respect to one another that the source reaches the prism with its face in contact with the film to be analyzed (backscattering mode).

According to another method of operation of the invention, a photodetector is centered on the axis of the beam reflected by the secant face, downstream from the thin film and from a diaphragm so that it operates in transmitted intensity analysis mode.

The positioning means may be provided, on its face demarcating the second wall of the thin film, with an element absorbing the incident beam for limiting the luminous reflected intensity.

In accordance with the scope of the invention, the luminous source and the prism are so arranged with respect to one another that the source traverses the thin film to be analyzed (forward scattered intensity analysis mode).

According to this embodiment of the invention, a photodetector may be placed on the axis of the transmitted beam, in order to receive a diffracted luminous signal.

A photodetector may furthermore be placed on the axis of the beam transmitted in order to analyze the luminous intensity transmitted by the sample to be analyzed.

The face of the prism in contact with the thin film is advantageously hollow to be as a receiving vessel for the sample to be analyzed.

The lower face of the positioning means is preferably convex so as to achieve a point of contact with the first wall demarcating the thin film.

The device according to the invention may also include a means allowing it to be operated at high temperatures and/or under high pressures.

The device according to the invention may thus be used to measure the grain size distribution or the viscosity measurable with light scattering, as well as the optical density or the turbidity. The measured grain size then ranges between 1 nm and 10 μm. When used in the diffraction field, the present invention allows grain sizes ranging between 10 μm and 600 μm, or even more, to be measured.

Black glass (used according to one embodiment of the invention) absorbs the incident beam of the monochromatic source after it has traversed the sample. This absorption avoids problems of reflection through the liquid/air interface. Without the black glass and according to the refractive index of the liquid, the reflected light may be 4% of the incident light.

The use of a prism shifts the entry spot of the monochromatic light beam and prevents the detector from observing it. In fact, according to one of the embodiments of the invention, the source light beam comes in on one of the vertical faces of the prism. It is totally reflected by the secant face, goes up vertically, crosses the sample, comes out on the other perpendicular face and is absorbed by the black glass arranged opposite the perpendicular face.

The detector, if it is in a fixed position, at 90° to the secant face, will thus observe the rays scattered at 135° in the case of a liquid and of a prism of identical refractive index. In the opposite case, the ray complies with the formula n1 sin i1=n2 sin i2, with n1 as the refractive index of the prism, i1 at the scattering angle with respect to the normal of the upper face normal of the prism and i2 equals 45°.

If the detector is placed under other conditions, the original scattering angle will be recalculated by means of the same formulas, while taking into account that the beam will undergo a second deviation by leaving the prism and entering the air.

The advantage of such an embodiment is thus to eliminate light reflections, to shift the entry spot of the laser beam and to create a thin sample layer, limiting thereby multiple scattering problems in a concentrated medium. The first measurements achieved gave excellent results for concentrations higher than 40% of solid matter.

The device according to the invention may be implemented either by adding an additional element to the known instruments of the state of the art, or by manufacturing a self-contained instrument.

According to an embodiment, the device in accordance with the invention includes a monochromatic source (such as a laser), a dioptric element glass prism, a resistant material or metal piece, having a hole in the center thereof and precisely placed on the horizontal surface of the prism and forming thereby a receiving vessel for the sample to be analyzed, and a cylinder mounted on a micropositioner, provided with a black glass disk at its lower end. This black disk has a slightly convex face to provide a contact point, for avoiding problems of the precision of the planar linearity of the two surfaces.

The laser beam focused by a lens mounted on an X and Y adjustable unit advantageously enters a glass prism of angle A=90°, parallel to the normal of the entry face. It is thus totally reflected upwards by the surface inclined at 45°, and leaves the prism at 90° to the upper horizontal surface. It traverses the sample to be analyzed. The sample is in direct contact with the upper surface of the prism.

Its thickness varies according to the precise vertical translation of a positioner provided with a glass piece having a black lower end.

It is well-known that the measurement of the intensity received by a photodetector placed on the axis of the incident beam, according to the thickness of the liquid film analyzed, provides:

The optical density for a colloid having an absorbent continuous phase and a non absorbent disperse phase.

The turbidity for a colloid having a non absorbent continuous phase and an absorbent disperse phase.

The invention allows the all of these measurements to be achieved, and it also enables determination of the grain size, the optical density and the turbidity of a very absorbent or even a black colloidal media. Measurement of the viscosity of the continuous phase may also be performed according to the present invention.

The measurements obtained according to the invention therefore open up applications in many fields. Viscosity measurements of engine oils may be cited as an example.

BRIEF DESCRIPTION OF THE DRAWINGS

Other features, details, improvements and advantages of the present invention will be clear from reading the description hereafter, given by way of non limitative examples, with reference to the accompanying drawings in which.

DESCRIPTION OF THE PREFERRED EMBODIMENTS

Figure 1:
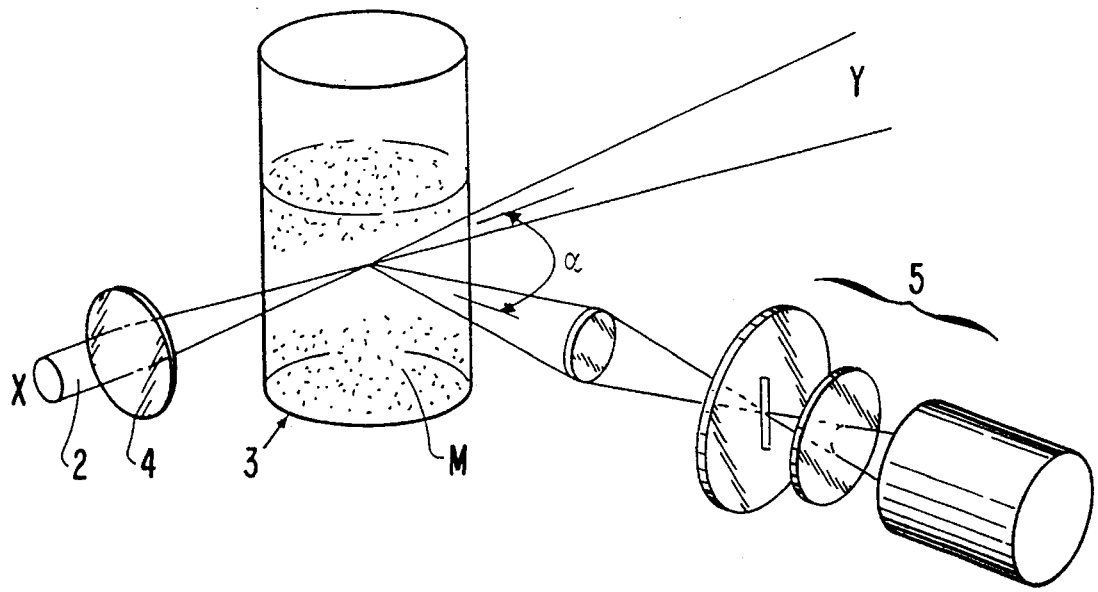
FIG. 1 diagrammatically shows a known acquisition device.
Figure 2:
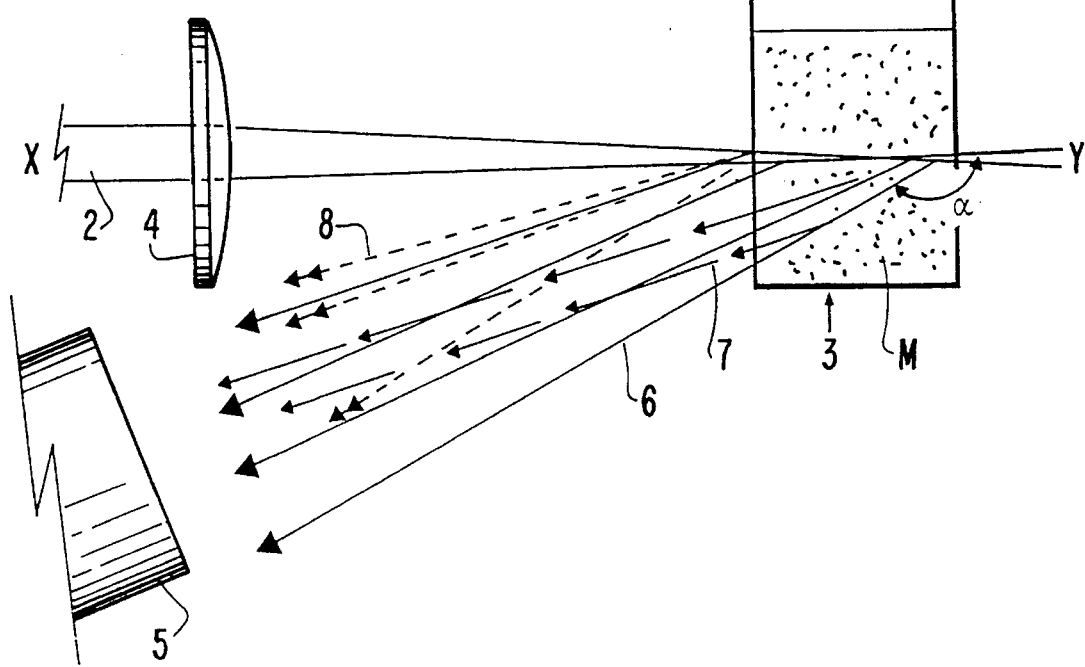
FIG. 2 shows the parasitic effects of backscatter measurements on these conventional instruments, FIG. 3 diagrammatically shows an embodiment in accordance with the invention.
Figure 3:
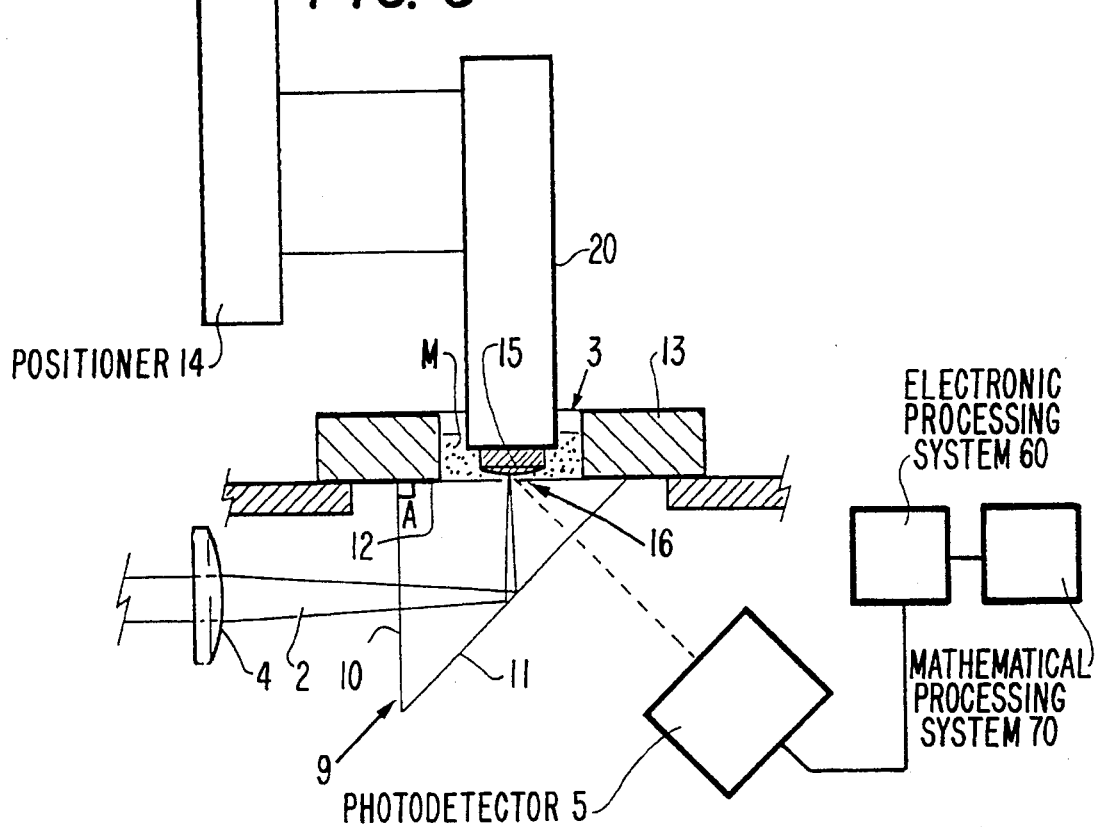

FIG. 3 is a cross-section of an embodiment of a device in accordance with the invention. It includes a dioptric element, in this case a prism 9 of angle A=90°, for example made of glass, intended for "refracting totally" laser beam 2. The different faces 10, 11, 12 of the prism 9 each form a dioptre, i.e. an optical surface separating two media of different refractive indexes.

Laser beam 2 enters through the normal of face 10, and it is totally reflected by the secant face 11 (because it forms an angle greater than or equal to the limit angle of refraction) and thus leaves through the normal of face 12. Consequently, the reflection of the beam on face 10 is thus very far from the observation volume on face 12.

According to this embodiment of the invention, one of the faces 12 of the prism is faced by a black metal piece 13 or by another solid material having a hole in its center which demarcates the sample containing the objects M to be analyzed, thus forming the vessel 3 receiving the sample.

The device further includes a vertical motion micropositioner 14 for vertically positions a piece 20 whose lower end is made of black glass 15. This black glass piece 15 has the same shape as and slightly smaller dimensions than receiving vessel 3. It may therefore fit into the vessel.

The black glass element 15 absorbs the incident beam and is intended for limiting the luminous intensity reflected. A "parasitic" intensity must not reach photodetector 5 because of the drawbacks cited above in connection with the prior art.

The end of the black glass element 15 is advantageously slightly convex in order to provide a contact point with face 12 and to avoid thereby problems of precision, planar linearity between two surfaces. The precise vertical translation provided positioner 14 causes the thickness of the sample to be analyzed to vary until a thin film 16 of several microns forms.

The luminous interactivity between the objects (M) contained in the sample is thus strongly decreased since few objects (M) will not be contained in the thin film 16. The experimenter will choose the finest thicknesses of film 16 for the smallest objects (M). It is thus obvious that the generation of this thin sample film 16 strongly decreases the multiple scattering effects described above.

Figure 4:
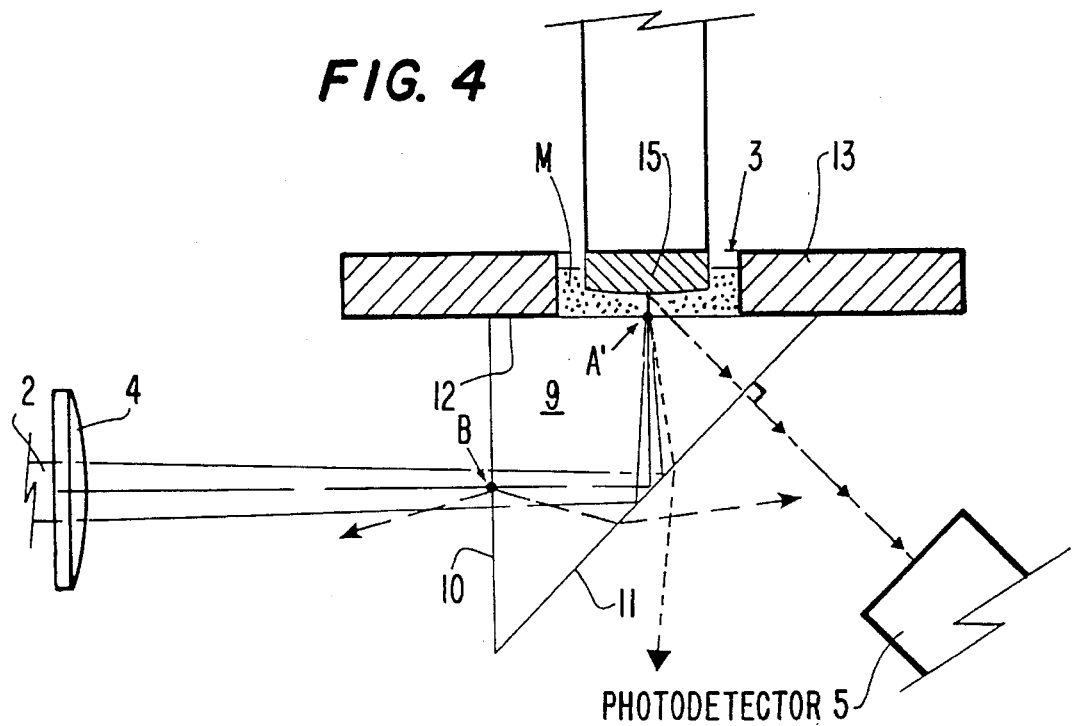
FIG. 4 diagrammatically shows the optical paths relative to the embodiment of FIG. 3.

FIG. 4, in accordance with the first embodiment of the invention, shows more precisely the optical paths. Lens 4 focuses beam 2 at point B located on face 10. Detector 5, firmly fixed, observes the sample volume located at point A'. It is located on an axis at 90° to face 11. Thus, in the case of a liquid whose refractive index is identical to that of the material making up the prism, the rays scattered by the objects (M) contained in the sample will undergo no deviation and the angle of observation with respect to the incident beam is here 135°.

In the case, for example, of an aqueous sample (of refractive index $n_1$=1.33 and of a glass prism of index $n_2$=1.5), the detector located in the same place as above observes the rays scattered at 127° to the incident beam. The value of this angle is given by the relation $n_1 \sin i_1 = n_2 \sin i_2$, that is $1.33 \sin i_1 = 1.5 (\sin 45°)$, that is $\sin i_1 = (1.5/1.33) \times (\sqrt{2}/2)$, which gives $i_1$=52.89, that is about an angle (180−52.9)=127.1° to the incident beam.

According to a particular embodiment, the vessel 3 containing the sample to be analyzed may be machined directly in the upper part of prism 9. It may therefore be hollowed in order to be used as a receiving vessel for the sample to be analyzed.

According to another embodiment, detector 5 may be mobile and thus observe point B according to various angles.

Without departing from the scope of the invention, the values of the angles of prism 9 may be different from those of the advantageous devices described in FIGS. 3 and 4. The luminous source will then be focused on the sample, and detector 5 will be so positioned that it may observe the backscattered rays, and the deviations in prism 9 which comply with the general law $n_1 \sin i_1 = n_2 \sin i_2$ will be taken into account.

Figure 5:
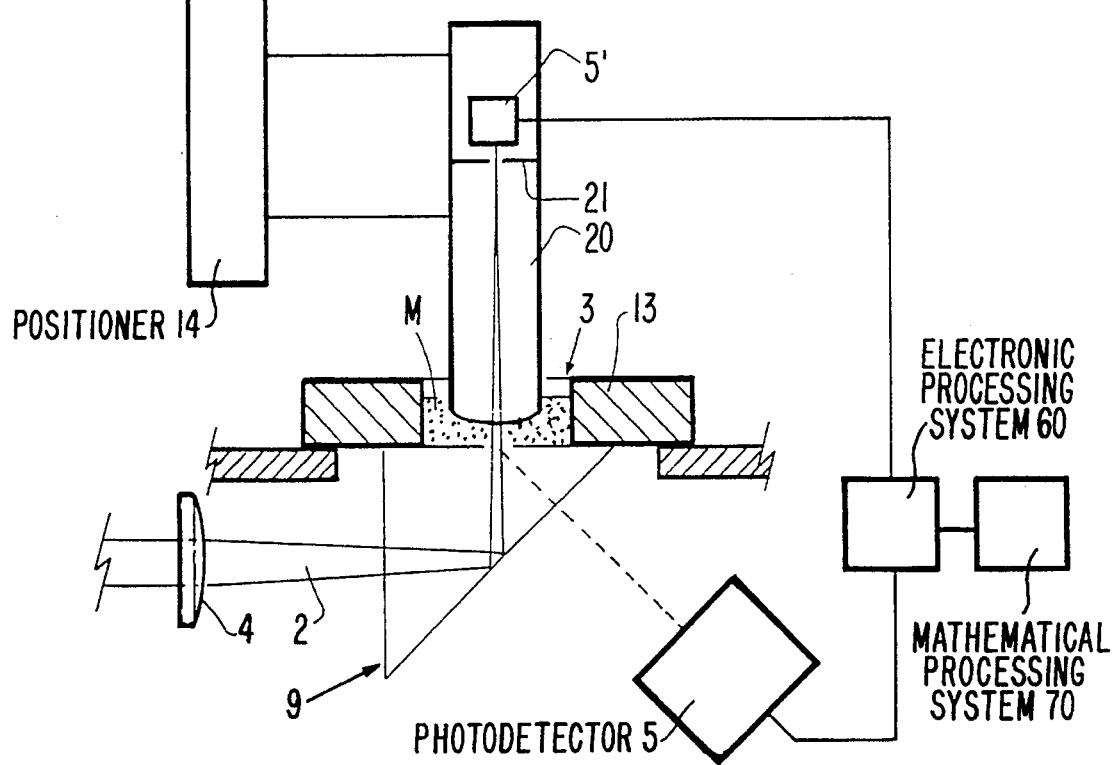
FIG. 5 diagrammatically shows another embodiment of the invention.

FIG. 5 illustrates another embodiment of the invention which differs from that described above mainly in the position and the method of operation of the photodetector.

According to the embodiment of FIG. 5, the incident beam, after it has tranversed the sample, is no longer absorbed (no black glass is used in this embodiment), but it tranverses the transparent element 20 prior to reaching a first photodetector 5' centered on the axis of the beam reflected by secant face 11.

A diaphragm 21 is preferably arranged just before photodetector 5' which operates thus in the transmitted intensity analysis mode. Photodetector 5' thus takes part in the determination of the optical density and/or of the turbidity of the thin film.

A second photodetector 5 is located, as in the first embodiment of the invention, on an axis perpendicular to the secant face 11 where it observes the luminous intensity scattered.

The two photodetectors 5 and 5' are connected to an electronic processing system 60 and/or to a mathematical processing system 70.

The function of the precise positioner 14 is very important here since it allows very precise control of the thickness of the thin film to be analyzed.

In fact, according to this embodiment of the invention, the luminous intensity detected and analyzed by photodetector 5' allows better characterization of the medium to be studied by obtaining additional information. The film thickness-laser power couple corresponding to the best grain size or viscosity analysis may thus be obtained for black or highly concentrated media.

Besides, the electronic processing system 60 allows notably the evolution in time of the tension delivered by photodetector(s) 5, 5' to be followed. Control of the intensity delivered by source 2 is jointly provided.

It is therefore permanently possible to check that the operating conditions are optimal, and notably that no thermal effect modifies locally the viscosity of the sample. In other words, the present invention allows any overheating likely to change locally the viscosity of the sample to be permanently avoided.

Figure 6:
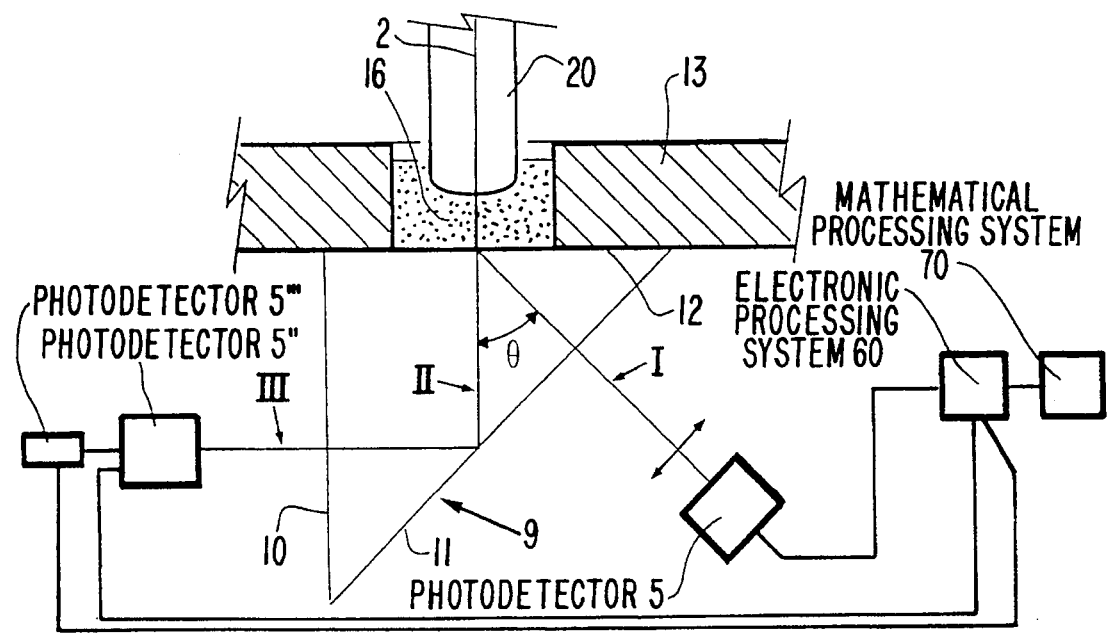
FIG. 6 diagrammatically shows yet another embodiment of the invention.

FIG. 6 illustrates another embodiment of the invention according to which the monochromatic source 2 tranverses successively element 20 (lengthwise), the thin film 16 to be analyzed and the face 12 of dioptric element 9.

From then on, the intensity scattered is detected by photodetector 5 located on an axis perpendicular to the secant face 11 of prism 9. The angle of observation between the axis of the scattered beam I falling on photodetector 5 and the axis of the original beam II is preferably stationary and has a lower value.

This method of operation is particularly well suited for a grain size analysis, by dynamic light scattering, of slightly absorbent colloids, which are weakly concentrated since photodetector 5 delivers then an amplitude better with a signal-to-noise ratio to processing systems 60, 70. The grain size range detected according to this method remains between about 1 nm and about 10 μm.

The luminous intensity II containing the signal diffracted by the sample is reflected at 90° by the secant face 11 towards photodetectors 5″, 5‴. The first photodetector 5′ observes the intensity of the signal diffracted, whereas the other photodetector 5‴ may be placed on the axis III of the beam transmitted in order to analyze the intensity transmitted by the sample 16 to be analyzed.

As in the embodiments of the invention described previously, electronic processing system 60 and/or mathematical processing system 70 are connected to photodetectors 5, 5′, 5‴ to allow the various signals to be processed.

Photodetectors 5′ and 5‴ allow grain sizes ranging between 10 μm and 600 μm, for moderately absorbent colloids, to be observed.

As a granulometer and a viscosimeter, the invention may operate at high temperatures and under high pressures, by any means known in the art.

As a viscosimeter, the invention does not subject the sample to any shear stress, unlike certain known devices.

Consequently, a significant advantage of the present invention lies in its non intrusive and non disturbing character of the sample to be analyzed.

We claim:

1. A device for measuring intensity of light scattered by a film of a colloidal media to be analyzed comprising:

a monochromatic luminous source for emitting a luminous beam;

a conveying optical system for focusing the luminous beam on the film to be analyzed;

at least one photosensitive detector for detecting light scattered by the film, and producing an output signal; and a system for processing the output signal from the at least one photosensitive detector; and wherein the optical system includes a dioptric element placed in the luminous beam having a face supporting the film, a wall disposed on the face which forms a well containing the film, an element disposed at least partially within the well formed by the face and the wall for absorbing at least part of the luminous beam transmitted by the film, and a positioner for positioning the element relative to an axis extending orthogonally from the face to control a thickness of the film to be analyzed.

2. A device in accordance with claim 1 wherein:

the dioptric element includes a secant face which reflects the luminous beam to cause the luminous beam to traverse the film perpendicular to the face.

3. A device in accordance with claim 2 wherein:

one of the at least one photosensitive detector is placed on an axis perpendicular to the secant face to cause the one photosensitive detector to detect scattered light surrounding a focusing point of the luminous beam on the film.

4. A device in accordance with claim 1 wherein:

the dioptric element is a prism.

5. A device in accordance with claim 4 wherein:

the prism is hollowed to form the well containing the film to provide a receiving vessel for the film.

6. A device in accordance with claim 1 further comprising:

a second photosensitive detector disposed along an axis of the luminous beam downstream from the film; and a diaphragm with an aperture centered along the axis of the luminous beam between the second photosensitive detector and the film; and wherein the second photosensitive detector is responsive to a transmittal of the luminous beam through the film.

7. A device in accordance with claim 1 further comprising:

means disposed on the element for limiting reflection of the luminous beam from the element.

8. A device in accordance with claim 1 wherein:

the light detected by the at least on photosensitive detector is forward scattered.

9. A device in accordance with claim 8 further comprising:

a second photosensitive detector disposed on an axis of the luminous beam downstream of transmission of the luminous beam through the film for detecting the luminous beam after diffraction by the dioptric element.

10. A device in accordance with claim 8 further comprising:

a second photosensitive detector disposed on an axis of the luminous beam downstream of transmission of the luminous beam through the film for detecting the luminous beam transmitted by the film.

11. A device in accordance with claim 8 further comprising:

a second photosensitive detector disposed on an axis of the luminous beam downstream of transmission of the luminous beam through the film for detecting the luminous beam after diffraction by the dioptric element; and a third photosensitive detector disposed on the axis of the luminous beam downstream of transmission of the luminous beam through the film for detecting the luminous beam transmitted by the film.

12. A device in accordance with claim 1 wherein:

the element has a surface opposed to the film which is convex to provide a point of contact with the face.

13. A device in accordance with claim 1 further comprising:

means for operating the device at high temperature.

14. A device in accordance with claim 1 further comprising:

means for operating the device at high pressure.

15. A device for measuring intensity of light backscattered by a film of a colloidal media to be analyzed comprising:

a monochromatic luminous source for emitting a luminous beam;

a conveying optical system for focusing the luminous beam on the film to be analyzed;

at least one photosensitive detector for detecting light backscattered by the film, and producing an output signal; and a system for processing the output signal from the at least one photosensitive detector; and wherein the optical system includes a dioptric element placed in the luminous beam having a face supporting the film, a wall disposed on the face which forms a well containing the film, an element disposed at least partially within the well formed by the face and the wall for absorbing at least part of the luminous beam transmitted by the film, and a positioner for positioning the element relative to an axis extending orthogonally from the face to control a thickness of the film to be analyzed.

16. A device in accordance with claim 15 wherein:

the dioptric element includes a secant face which reflects the luminous beam to cause the luminous beam to traverse the film perpendicular to the face.

17. A device in accordance with claim 16 wherein:

one of the at least one photosensitive detector is placed on an axis perpendicular to the secant face to cause the one photosensitive detector to detect scattered light surrounding a focusing point of the luminous beam on the film.

18. A device in accordance with claim 15 wherein:

the dioptric element is a prism.

19. A device in accordance with claim 15 further comprising:

a second photosensitive detector disposed along an axis of the luminous beam downstream from the film; and a diaphragm with an aperture centered along the axis of the luminous beam between the second photosensitive detector and the film; and wherein the second photosensitive detector is responsive to a transmittal of the luminous beam through the film.

20. A device in accordance with claim 15 further comprising:

means disposed on the element for limiting reflection of the luminous beam from the element.

21. A device in accordance with claim 15 wherein:

the element has a surface opposed to the film which is convex to provide a point of contact with the face.

22. A device in accordance with claim 15 further comprising:

means for operating the device at high temperature.

23. A device in accordance with claim 15 further comprising:

means for operating the device at high pressure.

24. A method for measuring intensity of light scattered by a film of a colloidal media comprising:

providing a device having a monochromatic luminous source for emitting a luminous beam, a conveying optical system for focusing the luminous beam on the film to be analyzed, at least one photosensitive detector for detecting light scattered by the film, and producing an output signal, and a system for processing the output signal from the at least one photosensitive detector, the optical system including a dioptric element placed in the luminous beam having a face supporting the film, a wall disposed on the face which forms a well containing the film, an element disposed at least partially within the well formed by the face and the wall for absorbing at least part of the luminous beam transmitted by the film, and a positioner for positioning the element relative to an axis extending orthogonally from the face to control a thickness of the film to be analyzed;

passing the luminous beam through the film; and measuring a size distribution of particles in the film.

25. A method in accordance with claim 24 wherein:

the measured size distribution ranges between 1 nm and 10 μm in a diffusion field.

26. A method in accordance with claim 24 wherein:

the measured size distribution range between 10 μm and 600 μm in a diffraction field.

27. A method for measuring intensity of light scattered by a film of a colloidal media comprising:

providing a device having a monochromatic luminous source for emitting a luminous beam, a conveying optical system for focusing the luminous beam on the film to be analyzed, at least one photosensitive detector for detecting light scattered by the film, and producing an output signal, and a system for processing the output signal from the at least one photosensitive detector, the optical system including a dioptric element placed in the luminous beam having a face supporting the film, a wall disposed on the face forming a well containing the film, an element disposed at least partially within the well formed by the face and the wall for absorbing at least part of the luminous beam transmitted by the film, and a positioner for positioning the element relative to an axis extending orthogonally from the face to control a thickness of the film to be analyzed;

passing the luminous beam through the film; and measuring viscosity of the film.

28. A method in accordance with claim 27 wherein:

the film is a thixotropic liquid.

29. A method for measuring intensity of light scattered by a film of a colloidal media comprising:

producing a device having a monochromatic luminous source for emitting a luminous beam, a conveying optical system for focusing the luminous beam on the film to be analyzed, at least one photosensitive detector for detecting light scattered by the film, and producing an output signal, and a system for processing the output signal from the at least one photosensitive detector, the optical system including a dioptric element placed in the luminous beam having a face supporting the film, a wall disposed on the face forming a well containing the film, an element disposed at least partially within the well formed by the face and the wall for absorbing at least part of the luminous beam transmitted by the film, and a positioner for positioning the element relative to an axis extending orthogonally from the face to control a thickness of the film to be analyzed;

passing the luminous beam through the film; and measuring an optical density of the film.

30. A method for measuring intensity of light scattered by a film of a colloidal media comprising:

providing a device having a monochromatic luminous source for emitting a luminous beam, a conveying optical system for focusing the luminous beam on the film to be analyzed, at least one photosensitive detector for detecting light scattered by the film, and producing an output signal, and a system for processing the output signal from the at least one photosensitive detector, the optical system including a dioptric element placed in the luminous beam having a face supporting the film, a wall disposed on the face forming a well containing the film, an element disposed at least partially within the well formed by the face and the wall for absorbing at least part of the luminous beam transmitted by the film, and a positioner for positioning the element relative to an axis extending orthogonally from the face to control a thickness of the film to be analyzed;

passing the luminous beam through the film; and measuring turbidity of the film.

* * * * *